US010765708B2

(12) United States Patent
Brand-Garnys

(10) Patent No.: US 10,765,708 B2
(45) Date of Patent: Sep. 8, 2020

(54) FORMULATION AND TREATMENT FOR ACNE

(71) Applicant: JAO Beheer BV, Heel (NL)

(72) Inventor: Elzbieta Ewa Brand-Garnys, Nieuwerkerk aan den IJssel (NL)

(73) Assignee: JAO Beheer BV, Heel (NL)

( * ) Notice: Subject to any disclaimer, the term of this patent is extended or adjusted under 35 U.S.C. 154(b) by 0 days.

(21) Appl. No.: 15/369,660

(22) Filed: Dec. 5, 2016

(65) Prior Publication Data

US 2017/0143776 A1 May 25, 2017

Related U.S. Application Data

(63) Continuation of application No. 14/346,236, filed as application No. PCT/EP2012/068580 on Sep. 20, 2012, now abandoned.

(30) Foreign Application Priority Data

Sep. 21, 2011 (EP) .................................... 11182258

(51) Int. Cl.

| *A61K 35/74* | (2015.01) |
|---|---|
| *A61K 9/00* | (2006.01) |
| *A61K 47/24* | (2006.01) |
| *A61K 47/26* | (2006.01) |
| *A61K 9/06* | (2006.01) |
| *A61K 35/747* | (2015.01) |
| *A61Q 19/00* | (2006.01) |
| *A61K 8/99* | (2017.01) |
| *A61K 47/08* | (2006.01) |
| *A61K 8/49* | (2006.01) |
| *A61K 8/55* | (2006.01) |
| *A61K 47/18* | (2017.01) |
| *A61K 47/38* | (2006.01) |

(52) U.S. Cl.
CPC ............ *A61K 35/74* (2013.01); *A61K 8/4973* (2013.01); *A61K 8/553* (2013.01); *A61K 8/99* (2013.01); *A61K 9/0014* (2013.01); *A61K 9/06* (2013.01); *A61K 35/747* (2013.01); *A61K 47/08* (2013.01); *A61K 47/186* (2013.01); *A61K 47/24* (2013.01); *A61K 47/26* (2013.01); *A61K 47/38* (2013.01); *A61Q 19/00* (2013.01); *A61K 2800/85* (2013.01); *A61K 2800/874* (2013.01)

(58) Field of Classification Search
None
See application file for complete search history.

(56) References Cited

U.S. PATENT DOCUMENTS

| 3,458,915 | A | * | 8/1969 | Smith | ................. H01L 41/0833 |
|---|---|---|---|---|---|
| | | | | | 257/417 |
| 5,413,960 | A | * | 5/1995 | Dobrogosz | .......... C07D 319/06 |
| | | | | | 435/124 |
| 8,052,984 | B2 | | 11/2011 | Suvanprakorn et al. | |
| 2004/0037856 | A1 | | 2/2004 | Catroux et al. | |
| 2008/0188568 | A1 | | 8/2008 | Suvanprakorn et al. | |

FOREIGN PATENT DOCUMENTS

| DE | 29923627 | | 12/2000 | | |
|---|---|---|---|---|---|
| EP | 1967180 | | 9/2008 | | |
| EP | 2226078 | | 9/2010 | | |
| WO | 03/053376 | | 7/2003 | | |
| WO | 03/075868 | | 9/2003 | | |
| WO | WO 2011/036304 | * | 3/2011 | ............... | A21D 8/04 |
| WO | 2012/007584 | | 1/2012 | | |

OTHER PUBLICATIONS

Russell et al., American Family Physician, Jan. 2000 15:61(2): 357-365 (Year: 2000).*
Wolf et al., SOFW-Journal, vol. 140, Mar. 2014: pp. 2-9.*
Woresana® rye serum K712 , Product Brochure, retrieved from the internet Mar. 28, 2018: http://raw-materials.mckinleyresources.com/Asset/WORESANA-rye-serum-K712-TDS.pdf.*
Kerwin et al., J. Pharma. Sci., 97(8):2924-2935 (2008) (Year: 2008).*
Ritter, U., "Lactobacillus/rye flour ferment—Fermentierter Rogen—a multitalent der kosmetischen Natur- und Wirkstoffszene. Lactobacillus/rye flour ferment: fermented rye—a multitalent in the cosmetic nature and active ingredient scene," SOFW-Journal Seifen (2002) 128(10):56-59.
Williams, H.C. et al., "Acne vulgaris," The Lancet (2011) published online, 12 pages.
European Patent Office Search Report for Application No. EP11182258 dated Feb. 15, 2012 (7 pages).
International Search Report and Written Opinion for Application No. PCT/EP2012/068580 dated Dec. 7, 2012 (16 pages).
Ethoxylated Sorbitan Esters-Polysorbates, retrieved from thornleycompany.com, Oct. 6, 2015 :http ://www.thornleycompany.com/Ethoxylated-Sorbitan-Esters-Polysorbates/.
Maggio et al., Polysorbates, peroxides, protein aggregation, and immunogenicity—a growing concern, J. Excipients and Food Chem. vol. 3 (2), pp. 45-53, 2012.

* cited by examiner

*Primary Examiner* — Thomas J. Visone
(74) *Attorney, Agent, or Firm* — Casimir Jones, S.C.; Lisa V. Mueller

(57) ABSTRACT

The present invention relates to composition comprising *Lactobacillus* rye ferment, dialkylisosorbide and phospholipid. Preferably, the composition further comprises ethoxylated sorbitan fatty acid ester. The composition has been shown to be effective against infections of closed comedones. The invention further relates to a method of preparing the composition, to a roll-on applicator comprising the composition and to the use of the composition in treatment of closed comedones infections.

7 Claims, 1 Drawing Sheet

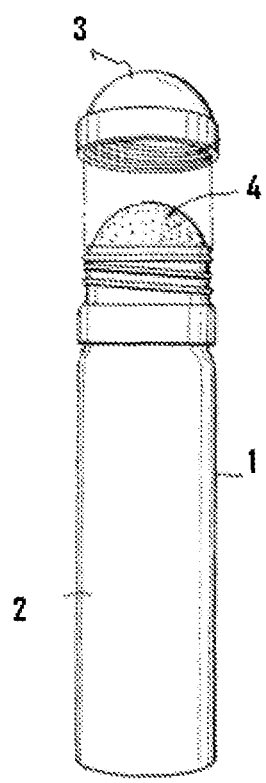

FORMULATION AND TREATMENT FOR ACNE

CROSS-REFERENCE TO RELATED APPLICATION(S)

This is a continuation of U.S. patent application Ser. No. 14/346,236, filed on Mar. 20, 2014, which is a U.S. national stage entry of International Patent Application No. PCT/EP2012/068580, filed on Sep. 20, 2012, which claims priority to European Patent Application No. 11182258.1, filed on Sep. 21, 2011, the entire contents of all of which are fully incorporated herein by reference.

TECHNICAL FIELD

The present invention relates to an anti-acne composition, to a method for preparing the composition, to an applicator comprising the composition and to a composition for use in treatment of acne.

BACKGROUND OF THE INVENTION

Acne is a skin disorder associated with *Propionibacterium acnes*, or *P. acnes* infections. It is clinically manifested by papules (red bumps), pustules and nodules.

Sebaceous glands are believed to become a growth matrix for *P. acnes*, an anaerobic gram-positive bacterium that is to a certain extent tolerant to oxygen. It feeds itself on the naturally occurring skin lipids and is therefore predominantly found in the sebaceous glands. *P. acnes* may become opportunistic if the conditions for growth are optimal which can happen when sebaceous glands get blocked due to excessive sebum production. The result is the formation of closed comedones, also called white heads. *P. acnes* produces enzymes that break down the wall of the sebaceous glands. This leads to folliculitis which may advance to skin breakage and scarring. In some cases these scars may also get infected.

Open comedones, also called black heads, represent another skin disorder associated with sebaceous glands. The glands remain open to the outside environment, allowing discharge and access through a pore.

Certain pharmaceutical products, such as oral contraceptives, may induce the occurrence of acne and particularly of infected closed comedones.

Different treatments have been proposed to resolve acne. Careful and thorough skin cleansing may be advantageous for open comedones. However, particularly for closed comedones this is insufficient as illustrated by quick reoccurrence of the infection.

Examples of anti-acne medications are as follows:

Retinoids (vitamin A derivatives) are effective by increasing skin cell turnover and promoting the extrusion of the plugged material in hair follicles. However, it may take time to see improvements. Accutane is a systemically administered oral retinoid.

Antibiotics have a direct effect on the bacteria but need to be administered systemically while potential side-effects may be associated with timing of food intake, interference with teeth growing and photosensitivity.

Benzoyl peroxide is only allowed on the market in the USA and is effective due to its oxidative power, but may leave the skin uncomfortably dry and flaky, cause photosensitivity, and interact with other acne treatments like retinoids. Furthermore, the oxidative power of benzoyl peroxide may extend to other molecular entities that are present in the skin and that are sensitive to oxidation.

Salicylic acid clears the pores but may cause skin irritation and in virtually all cases the chance of recidivism is high. This can also be said about essential oils such as clove oil, oil of wintergreen and chaulmoogra oil.

Use of *Lactobacillus* rye ferment has been described in several patent applications. WO 03/053376 discloses *Lactobacillus* rye ferment for use in skin treatment, either as face or body mask, lipstick, hair shampoo or conditioner. Example 2 illustrates the use of this ingredient as facemask in a small patient group with open comedones and inflamed scar tissue. Example 4 refers to the use of raw or pasteurized *Lactobacillus* rye ferment material per se as facemask in acne treatment and illustrates poor in-vivo activity.

EP 2226078 discloses formulations comprising *Lactobacillus* rye ferment and a penetration enhancer for anti-fungal treatment of nails and feet.

DE 29923627 discloses various methods of preparing *Lactobacillus* rye ferment. The ingredient has been suggested for skin peeling, removing fat, and increasing facial blood flow.

WO 03/075868 uses *Lactobacillus* DSM 6037 and *Lactobacillus* DSM 6129 for the preparation of *Lactobacillus* rye ferment. The ingredient obtained has been suggested for use in unaltered form as treatment for the skin, for instance as facemask, body mask or bath additive. The ferment can also be added to face and body masks, lipsticks, shampoos or conditioners.

Despite available treatments, acne infections, especially those associated with closed comedones, remain an undertreated medical condition that particularly affects many adolescents and young adults, most often undermining their self-esteem.

SUMMARY OF THE INVENTION

Surprisingly, we have found a way to improve acne treatment and overcome one or more of the above and other problems of the prior art. In particular, we have found a way to address difficult to treat infected closed comedones that are notorious with teenagers.

BRIEF DESCRIPTION OF THE DRAWING(S)

The FIGURE illustrates a roll-on applicator comprising a container (1) that holds the composition of the invention (2). Cap (3) covers applicator ball (4).

In one aspect, the present invention relates to a composition comprising *Lactobacillus* rye ferment, dialkylisosorbide and phospholipid. Preferably, the composition further comprising ethoxylated sorbitan fatty acid ester.

Preferably, the phospholipid is phosphatidylcholine. Preferably, the phospholipid is unsaturated. Preferably, the ethoxylated sorbitan fatty acid ester is unsaturated. Preferably, the sorbitan fatty acid ester is polysorbate 80.

Preferably, the composition further comprises hydroxyethylcellulose and hydroxylpropylcellulose, each at a level of from 0.01 to 3% by weight.

Preferably, the composition further comprises an osmolyte selected from the group of betaines and the group of nonionic osmolytes. Preferably, the composition comprises an osmolyte at a level of from 0.1 to 5% by weight of the composition.

In another aspect, the present invention relates to a method of preparing a composition comprising *Lactobacillus* rye ferment by mixing the ferment with dialkylisosorbide and phospholipid. In a preferred method, ethoxylated sorbitan fatty acid ester is added.

In a further aspect, the present invention relates to a roll-on applicator comprising a composition according to the invention. Preferably, the composition in the applicator further comprises ethoxylated sorbitan fatty acid esters.

In a further aspect, the present invention relates to a composition comprising *Lactobacillus* rye ferment, dialkylisosorbide and phospholipid for use in treatment of infected comedones. Preferably, the composition further comprises ethoxylated sorbitan fatty acid esters.

Surprisingly, we have found that the problems of the prior art can be addressed by the presently claimed composition. In fact, we have found that even *P. acnes* infected closed comedones can be effectively treated without the use of harsh ingredients, and within a short treatment time period. We have further found that the particular composition of the invention results facial transdermal transportation of high levels of active in a short period of time, resulting in high efficacy against bacteria and in particular *P. acnes*.

We have found that fermented cereal grain has excellent activity specifically against *P. acnes* in-vitro. However, we have surprisingly found that there is no (or very limited) in-vivo activity against infected closed comedones when applied directly on the affected skin. Subsequently, we have surprisingly found that compositions according to the present invention have good in-vivo efficacy offering a treatment without the negatives of the products of the prior art. Without wishing to be bound by any theory, we believe that quick penetration of high levels of the composition of the invention effectively eradicates *P. acnes*.

The composition according to the invention comprises *Lactobacillus* rye ferment. Preferably, the bacteria are *Lactobacillus* species. Examples of suitable *Lactobacillus* species are *Lactobacillus* DSM 6037 and *Lactobacillus* DSM 6129. Preferably, fermentation takes place under conditions as specified in DE 2923627 and in WO 03/053376. A preferred compound for use in the present invention is WORESANA® serum, a water-based, slightly viscous, transparent solution. WORESANA® is a registered trademark of Woresan GmbH.

In a kinetic challenge test, we exposed *P. acnes* to *Lactobacillus* rye ferment and measured a log 5 reduction over time. Preferably, compositions of the present invention preferably comprise *Lactobacillus* rye ferment at a level of at least 40%, more preferably at least 50%, most preferably at least 60%. Considering the presence of other ingredients, the composition preferably comprises at most 95%, and more preferably at most 90% by weight of *Lactobacillus* rye ferment.

Although high in vitro activity has been demonstrated, *Lactobacillus* rye ferment has been found to be ineffective in-vivo against closed comedone infections. Surprisingly, Applicants believe that *Lactobacillus* rye ferment is effective in-vivo against closed comedones, when topically applied in combination with the penetration enhancers of the invention, as discussed below. Surprisingly, we have found that penetration of *Lactobacillus* rye ferment can be synergistically improved by including penetration enhancers, leading to high efficacy against *P. acnes*, even when present in difficult to treat closed comedone infections. According to the invention, the composition comprises dialkylisosorbide and phospholipid as penetration enhancers.

The composition of the present invention comprises dialkylisosorbide. A preferred dialkylisosorbide is dimethylisosorbide (DMI). Dimethylisosorbide is supplied by Croda Oleochemicals under the trademark Arlasolve DMI®.

The composition of the invention preferably comprises at least 0.1%, more preferably at least 0.5%, most preferably at least 1.2% and preferably up to 30%, more preferably 8%, most preferably up to 5% by weight of dialkylisosorbide.

The composition of the present invention comprises phospholipid. Preferably, the phospholipid is derived from glycerophosphoric acid. Preferably, the phosphoric acid moiety of glycerophosphoric acid is esterified with choline, inositol, galactose, ethanolamine, or serine and more preferably with choline. Preferably, the glycerophosphoric acid is esterified with two fatty acid moieties. Preferably, the fatty acid moieties are—independently—selected from fatty acids with 2-30 carbon atoms. The fatty acid moieties may be straight or branched. Preferably, at least one of the fatty acid moieties is unsaturated.

We have found that this leads to improved penetration. Preferably, the phosphatidylcholine is esterified with palmitic acid, stearic acid and/or oleic acid, more preferably oleic acid. A preferred phospholipid of the invention is phosphatidylcholine as supplied by Lipoid under the trademark Phospholipon 85G®. The composition of the invention preferably comprises at least 0.01%, more preferably at least 0.05%, most preferably at least 0.1% and preferably up to 2%, more preferably 1%, most preferably up to 0.4% by weight of phospholipid.

The composition of the present invention preferably comprises ethoxylated sorbitan fatty acid ester. Preferably, the ethoxylated sorbitan fatty acid ester is prepared by esterification of sorbitol with the fatty acid, whereby the sorbitol unit rearranges to a sorbitan unit, followed by ethoxylation with ethylene oxide. Preferably, the sorbitan fatty acid ester carries from one to three fatty acid moieties. Preferred examples of sorbitan fatty acid esters include one fatty acid moiety, one-and-a-half fatty acid moieties or three fatty acid moieties and more preferably one fatty acid moiety. It is noted that these values are averages and that a mix of sorbitan fatty acid esters with random distribution of fatty acids per sorbitan molecule will be present as has been well established in the art. Preferably, the fatty acid moiety has a chain length of two to 30 carbon atoms. Preferably, the fatty acid moiety is unsaturated. We have found that this leads to improved penetration. A preferred fatty acid moiety originates from oleic acid (cis-9-octadecenoic acid). Preferably, the oleic acid is from vegetable origin which is usually accompanied by small amounts of saturated and other unsaturated fatty acids. An example is Priolene 6900® as supplied by Croda Oleochemicals. Preferably, the sorbitan fatty acid ester is ethoxylated. Preferably, the sorbitan fatty acid ester is ethoxylated with 1 to 200 units of ethylene oxide, more preferably at least 2 to 120 units of ethylene oxide, most preferably at least 4 to 40 units of ethylene oxide and particularly preferred with an average of 20 units of ethylene oxide units. The ethylene oxide units are preferably randomly distributed amongst the available hydroxyl groups of the sorbitan fatty acid ester. It will be understood that the cited values are averages and that a mix of sorbitan fatty acid ester compounds will be present representing a random distribution.

Preferred ethoxylated sorbitan fatty acid esters are polysorbate 80 (PEG-20 sorbitan oleate, comprising one unit of oleic acid), polysorbate 83 (PEG-20 sorbitan sesquioleate, comprising one-and-a-half units of oleic acid) and polysorbate 85 (PEG-20 sorbitan trioleate, comprising three units of oleic acid). Most preferred is polysorbate 80. An example is Tween 80® which is marketed by Croda Oleochemicals.

The composition of the invention preferably comprises at least 0.05%, more preferably at least 0.1%, most preferably at least 0.2% and preferably up to 3%, more preferably 1.5%, most preferably up to 0.6% by weight of sorbitan fatty acid ester.

Further examples of penetration enhancers that may be included in compositions of the invention are low molecular weight alcohols (such as ethanol, 1-propanol, isopropanol), fatty alcohols (such as caprylyl alcohol, capryl alcohol, lauryl alcohol), monoterpenoids (such as limonene, linalool, eugenol), dimethyl sulfoxide (DMSO), β-cyclodextrines, dimethyl formamide (DMF), cyclopentadecalactone, alkyl-2-(N,N-disubstituted amino)-alkanoate ester and 2-(n-nonyl)-1,3-dioxolane. Preferred levels are from 0.01-10.0% by weight.

The composition according to the invention preferably comprises solvent, more preferably hydrophilic solvent. Solvents are preferably selected from water, low molecular weight alcohols with 2-10 carbon atoms (short chain alcohols), esters of molecular weight less than 150 Dalton (low molecular weight carboxylic acid esters), low molecular weight ketones of less than 50 Dalton, 1,2- and 1,3-glycols such 1,2- and 1,3-propylene glycol, 1,3-butylene glycol, 1,2-pentanediol, 1,2-hexanediol, 1,2-octanediol, polyethylene glycols comprising 1-150 units of ethylene oxide, and polyols such as glycerol. More preferably, the solvent is selected from water and pentylene glycol. Particularly preferred is a mixture of water and glycol, especially pentylene glycol (1,2-pentanediol), simultaneously enabling microbiological control.

Preferably, compositions according to the present invention comprise at least 1%, more preferably at least 5%, most preferably at least 0% and preferably at most 60%, more preferably at most 40% most preferably at most 30% by weight of solvent.

The composition according to the invention preferably comprises thickening agent. The thickening agent facilitates easy application of the composition on the skin and particularly on the infected closed comedones. The thickening agent is preferably selected from the group of natural polysaccharides (xanthan gum, sclerotium gum, locust bean gum, guar gum, tragacanth gum, alginates, carrageenan), cellulose ethers (methylcellulose, hydroxyethylcellulose, hydroxypropyl cellulose, hydroxypropyl methylcellulose, hydrophobised cellulose ethers), homo and copolymers of acrylic acid and methacrylic acid, blockcopolymers of ethylene oxide and propylene oxide (also known as poloxamers). Preferably, compositions according to the present invention comprise from 0.2 to 5% by weight of thickening agent or mixtures of thickening agents.

Preferably, compositions of the invention comprise a combination of hydroxyethylcellulose (HEC) and hydroxypropylcellulose (HPC). HEC provides low viscous gels with a high yield stress while HPC provides medium to high viscous gels, usually with a low yield stress value; the yield stress value determines the suspending power of gels & emulsions. In addition, the combination is beneficial as the polymer combination reduces the shine of the composition when applied as a film to the skin, rendering the composition more esthetically and socially acceptable. HEC is preferably used at a level of from 0.01 to 3%, more preferably from 0.05 to 1%, most preferably from 0.1 to 4% by weight of the composition. HPC is preferably used at a level of from 0.01 to 3%, more preferably from 0.05 to 1%, most preferably from 0.1 to 4% by weight of the composition.

Using the thickening agent, the pseudoplastic constant (ψ) according to Herschel-Bulkley of the composition is preferably set between 0.2 and 0.8, more preferably between 0.3 and 0.7, most preferably between 0.4 and 0.6, while the viscosity of the composition is preferably set between 200 and 60000 cPs, i.e. from low viscous flowing gel to very high viscous stand-alone gel.

The composition according to the invention preferably comprises an osmolyte, which may also be called an osmoprotectant. Preferably, osmolytes either have a positive and a negative charge in the same molecule or are of a nonionic nature. Preferred osmolytes are selected from betaine and the group of polyols and non-reducing sugars. Preferred betaines are trimethylglycine, trimethyl choline, trimethyl choline sulphate, trimethyl alanine, dimethyl sulfopropionate (DMSP), N,N-dimethylproline (strachydrine), N,N-dimethylhydroxyproline, ectoine, and hydroxyectoin.

Preferred polyols and non-reducing sugars are trehalose, mannitol, glycerol, glycosylglycerol, inuline, xylitol, inositol and tri- and polysaccharides. The most preferred osmolyte for compositions of the invention is trimethylglycine. Preferably, the osmolyte is present at a level of at least 0.01%, more preferably at least 0.2%, most preferably at least 0.5% and preferably at most 10%, more preferably at most 5% and most preferably at most 2% by weight of the composition.

Preferably, the method of preparing compositions of the invention comprises mixing *Lactobacillus* rye ferment with dialkylisosorbide and phospholipid. Preferably, ethoxylated sorbitan fatty acid esters is added. Preferably, the penetration enhancers are premixed and subsequently added to the *Lactobacillus* rye ferment. Preferably, the thickening agent/rheological additive is first dispersed in *Lactobacillus* rye ferment under agitation. Preferably, the osmolyte is dissolved in the end product. Preferably, the pH of the composition is set at 4.5 to 5 using an aqueous sodium hydroxide or an aqueous citric acid solution.

Preferably, the composition of the invention is applied using a roll-on applicator. As an non-limiting example, the FIGURE refers to a roll-on applicator comprising container (1) that holds the composition of the invention (2). Cap (3) covers applicator ball (4) that can roll but is held in place by inward extensions from the wall of the container. By tilting container (1), composition (2) wets applicator ball (4). By applying rolling applicator ball against the affected skin, composition (2) is applied to the infected closed comedones.

Surprisingly, we have found that a composition comprising *Lactobacillus* rye ferment, dialkylisosorbide and phospholipid is effective for use in treatment of acne. We have found that the composition is effective in the treatment of infected open comedones and particularly surprisingly of infected closed comedones. Infected closed comedones have been found to be difficult to treat, yet they affect many adolescents and young adults undermining their self-esteem.

The composition of the invention is particularly suitable for application on the facial skin. Acne infections represents themselves on the facial skin, sometimes also affecting the neck and back. The composition is particularly suitable for topical application on the facial skin. Note that the facial skin has a very different build up as compared to for instance the skin of the foot sole which is covered with callus (i.e. layers of dead skin cells) having a very different, non-comparable penetration profile. Also, the skin of the face is more sensitive, always in view and exposed to the environment.

Without wishing to be bound by any theory, we believe that the composition of the present invention is particularly suitable for treatment of bacteria, providing exposure to a high dose of active during a short period of time. These kinetic factors are for instance very different from treatment of fungus which requires long exposure to medication to be effective (for instance 1 month or 6 months) while the high peak dose as used in treatment of bacteria is also not applicable.

Consequently, the invention relates to a composition comprising *Lactobacillus* rye ferment, dialkylisosorbide and phospholipid for use in treatment of infected comedones and particularly closed comedones. Preferably, the composition further comprising ethoxylated sorbitan fatty acid esters.

The present invention further relates to treatment of acne and especially infected closed comedones, by administration of a composition comprising *Lactobacillus* rye ferment, dialkylisosorbide and phospholipid. Preferably, the composition is applied topically. Preferably, a roll-on applicator is used. We have found that use of a roll-on applicator allows for gentle application of the composition to the affected skin areas while avoiding to generate too much pressure on the comedones, particularly the closed comedones. Preferably, the composition further comprises ingredients as indicated above. We have found that the composition is particularly effective in treating *P. acnes* infections.

The following non limiting examples illustrate the invention.

EXAMPLES

Example 1

The following compositions with different combinations of penetration enhancers were studied in-vitro in a Franz diffusion cell, an in-vitro representation of in-vivo activity of the active ingredient. The cell consists of two compartments that are separated by a membrane, for instance a pig skin. A composition with an active ingredient is applied to one compartment and the concentration of the active is measure in the other compartment over time. Level of transport as well as the speed are indicative for in-vivo activity. The following base composition was used:

| Ingredient | % by weight |
|---|---|
| *Lactobacillus* Rye Ferment (WORESANA ® serum; Woremed) | 65.00 |
| Pentylene Glycol (Hydrolite ® 5; Symrise) | 10.00 |
| Trimethylglycine (Betafin BP20 ®; Danisco Finnfeeds) | 1.20 |
| Hydroxyethylcellulose (Natrosol ®; Ashland) | 0.20 |
| Hydroxypropylcellulose (KlucelU ®; Ashland) | 0.10 |
| Penetration enhancers - as indicated below | variable |
| Demineralized water | ad. 100 |

The following penetration enhancers were tested with results indicated:

| Ingredient (% weight) | transport extent | 50% transport time |
|---|---|---|
| 1. none | 0% | infinite |
| 2. 3.2% dimethylisosorbide (DMI) | 45 | 16 minutes |
| 3. 0.25% phosphatidylcholine (PC) | 11 | 120 minutes |
| 4. 0.35% polysorbate 80 (PS) | 4 | >200 minutes |
| 5. 3.2% DMI & 0.25% PC | 21 | 85 minutes |
| 6. 3.2% DMI & 0.35% PS | 51 | 14 minutes |
| 7. 0.25% PC & 0.35% PS | 35 | 120 minutes |
| 8. 3.2% DMI & 0.25% PC & 0.35% PS | 82 | <2 minutes |

This experiment shows that *Lactobacillus* rye ferment without any penetration enhancer is inactive in the Franz diffusion test. Addition of one penetration enhancer increases level of active transport and decreases transport time for 50% of the active. It is noted that using higher levels of penetration enhancer does not result in higher or faster active transportation across the membrane.

The test results clearly show the surprising synergistic effect of a combination of two different penetration enhancers. Moreover, a combination of three penetration enhancers leads to even better results.

It can be concluded that combinations of different penetration enhancers unexpectedly leads to the high transportation levels and short transportation time. It will be understood that the activity of *P. acnes* in closed comedones will be optimally suppressed with compositions comprising two and preferably three or more synergistically working penetration enhancers.

In-vivo inactivity of the *Lactobacillus* rye ferment composition without penetration enhancers was confirmed in a clinical trial of five subjects suffering from closed comedone infections. The composition was applied two times per day for ten consecutive days to the face but no improvements were observed illustrating that this composition does not treat closed comedone infections.

Example 2

A composition according to the invention with the following ingredients was prepared as indicated:

| Ingredient | % by weight |
|---|---|
| *Lactobacillus* Rye Ferment (WORESANA ® Serum; Woremed) | 65.00 |
| Demineralized water | 19.70 |
| Pentylene Glycol (HydroliteU ® 5; Symrise) | 10.00 |
| Dimethylisosorbide (Arlasolve DMI ®; Croda Oleochemicals) | 3.20 |
| Trimethylglycine (Betafin BP20 ®; Danisco Finnfeeds) | 1.20 |
| Polysorbate 80 (Tween 80 ®; Croda Oleochemicals) | 0.35 |
| Phosphatidylcholine (Phospholipon 85G ®; Lipoid) | 0.25 |
| Hydroxyethylcellulose (Natrosol ®; Ashland) | 0.20 |
| Hydroxypropylcellulose (Klucel ®; Ashland) | 0.1 |

Hydroxyethylcellulose and hydroxypropylcellulose were dispersed in the mixture of WORESANA® and water using a propeller mixer. As soon as the polymers were effectively wetted the propeller mixer was exchanged for a planetary mixer. Stirring was continued for 2 hours; a low viscous yellowish-brownish flowing gel was obtained, free of polymer aggregates.

Pentylene glycol, dimethylisosorbide, phosphatidylcholine and polysorbate 80 were mixed. Slight heating to 30-35° C. accelerated the dissolution of phosphatidylcholine. The mixture was added to the gel and mixed until homogeneous.

Betaine was added as crystals and quickly dissolves in the gel. The pH of the gel was set at 4.5-5.0 using either a 50% aqueous citric acid solution or 18% aqueous sodium hydroxide solution. The viscosity of the composition was 600-900 cPs (Brookfield Viscosity meter DV-II+ Programmable, or higher; spindle 3, 20 rpm, 20° C.).

The obtained gel was subjected to microbiological analysis after 24 hrs and satisfied a plate count of <10 CFU/g (Colony Forming Units); the absence of pathogens was confirmed.

Example 3

The following gel was formulated using the method of example 2:

| Ingredient | % by weight |
| --- | --- |
| *Lactobacillus* Rye Ferment (WORESANA ®  Serum; Woremed) | 65.00 |
| Demineralized water | 19.35 |
| Pentylene Glycol (Hydrolite ® 5; Symrise) | 10.00 |
| Dimethylisosorbide (Arlasolve DMI ®; Croda Oleochemicals) | 3.20 |
| Trimethylglycine (Betafin BP20 ®; Danisco Finnfeeds) | 1.20 |
| Polysorbate 80 (Tween 80 ®; Croda Oleochemicals) | 0.35 |
| Hydroxyethylcellulose (Natrosol ®; Ashland) | 0.30 |
| Hydroxypropylcellulose (Klucel ®; Ashland) | 0.25 |
| Phosphatidylcholine (Phospholipon 85G ®; Lipoid) | 0.25 |

The viscosity of the gel was 2000-2800 cPs (Brookfield Viscosimeter DV-II+ Programmable, or higher; spindle 4, 20 rpm, 20° C.).

In the above formulations, hydroxypropylcellulose was replaced by hydroxypropyl methylcellulose (Benecel®; Ashland) and the viscosity increased to 6000-8000 cPs (Brookfield Viscosimeter DV-II+ Programmable, or higher; spindle 5, 20 rpm, 20° C.).

Example 4

The composition of example 2 was tested in 22 patients suffering from infected closed comedones. The composition was applied with the roll-on applicator of FIG. 1 twice daily for 12 days. Results were rated on days 1, 2, 3, 4, 5, 8, 9, 10, 11 and 12. The following visual scale was used:

| Visual observation | rating |
| --- | --- |
| No improvement: | 0-1 |
| Clearly noticeable improvement: | 2-3 |
| Good improvement: | 4-6 |
| Excellent improvement; | 7-9 |
| Complete recovery: | 10 |

The following results were obtained:

| | | | treatment day | | | | | | | |
| --- | --- | --- | --- | --- | --- | --- | --- | --- | --- | --- |
| Nr | gender | age | 1 | 2 | 3 | 4 | 5 | 8 | 9 to 12 | result |
| 1 | Female | 15 | 0 | 0 | 1 | 4 | 8 | 10 | 10 | positive |
| 2 | Female | 15 | 3 | 6 | 8 | 10 | 10 | 10 | 10 | positive |
| 3 | Female | 17 | 0 | 4 | 5 | 8 | 10 | 10 | 10 | positive |
| 4 | Female | 18 | 4 | 5 | 7 | 9 | 10 | 10 | 10 | positive |
| 5 | Female | 21 | 2 | 5 | 6 | 6 | 8 | 10 | 10 | positive |
| 6 | Female | 23 | 3 | 4 | 6 | 8 | 9 | 10 | 10 | positive |
| 7 | Female | 24 | 0 | 0 | 0 | 0 | 0 | 0 | 0 | negative |
| 8 | Female | 24 | 0 | 3 | 7 | 9 | 10 | 10 | 10 | positive |
| 9 | Female | 26 | 0 | 4 | 7 | 8 | 10 | 10 | 10 | positive |
| 10 | Female | 27 | 0 | 0 | 4 | 6 | 8 | 10 | 10 | positive |
| 11 | Female | 29 | 0 | 3 | 5 | 6 | 8 | 10 | 10 | positive |
| 12 | Male | 14 | 3 | 6 | 9 | 10 | 10 | 10 | 10 | positive |
| 13 | Male | 14 | 0 | 3 | 5 | 7 | 9 | 10 | 10 | positive |
| 14 | Male | 15 | 0 | 4 | 8 | 10 | 10 | 10 | 10 | positive |
| 15 | Male | 15 | 0 | 5 | 8 | 10 | 10 | 10 | 10 | positive |
| 16 | Male | 17 | 0 | 0 | 1 | 0 | 5 | 10 | 10 | positive |
| 17 | Male | 18 | 0 | 4 | 7 | 8 | 10 | 10 | 10 | positive |
| 18 | Male | 19 | 2 | 3 | 7 | 9 | 10 | 10 | 10 | positive |
| 19 | Male | 21 | 3 | 4 | 7 | 8 | 10 | 10 | 10 | positive |
| 20 | Male | 24 | 0 | 4 | 8 | 10 | 10 | 10 | 10 | positive |
| 21 | Male | 26 | 0 | 2 | 6 | 8 | 9 | 10 | 10 | positive |
| 22 | Male | 30 | 0 | 0 | 4 | 5 | 8 | 10 | 10 | positive |

Treatment of infected closed comedones was effective in 21 out of 22 subjects. For 5 subjects, the efficacy end point was achieved after 4 days, for 7 subjects after 5 days and for 8 subjects after 8 days. No adverse effects were reported.

Clinical benefits were maintained for a period of at least 1 week after the conclusion of the trial. Further illustrating the efficacy of the composition of the invention in overcoming infected closed comedones, only one patient indicated no interest in the product while 2 patients indicated that they might buy the product and 19 patients indicated that they would buy the product if commercially available.

It can be concluded that the composition with a combination of penetration enhancers according to the invention shows surprising synergistic efficacy in treating infected closed comedones offering an excellent treatment options for adolescents and young adults.

The invention claimed is:

1. A method of treating *Propionibacterium acnes* infected comedones, the method comprising: administering a composition comprising:
    from 40 to 65% by weight of *Lactobacillus* rye ferment;
    from 1.2 to 5% by weight of dimethyl isosorbide;
    from 0.1 to 0.4% by weight of phosphatidylcholine; and
    from 0.2 to 1.5% by weight of polysorbate 80.

2. The method according to claim 1, the composition further comprising hydroxyethylcellulose and hydroxypropylcellulose, each at a level of from 0.01 to 3% by weight.

3. The method according to claim 1, the composition further comprising an osmolyte selected from betaines and nonionic osmolytes at a level of from 0.1 to 5% by weight of the composition.

4. The method according to claim 1, wherein the composition is administered to the infected comedones with a roll-on applicator.

5. The method according to claim 1, wherein the composition is applied topically.

6. The method according to claim 1, wherein the *Lactobacillus* is selected from *Lactobacillus* DSM 6037, *Lactobacillus* DSM 6129, and mixtures thereof.

7. The method according to claim 1, wherein the composition comprises from 40 to 65% by weight of *Lactobacillus* rye ferment;
    3.2% by weight of dimethyl isosorbide;
    0.25% by weight of phosphatidylcholine; and
    0.35% by weight of polysorbate 80.

* * * * *